US00PP35316P2

(12) United States Plant Patent
Ranney et al.

(10) Patent No.: US PP35,316 P2
(45) Date of Patent: Aug. 15, 2023

(54) ***HYDRANGEA* PLANT NAMED 'NCHP1'**

(50) Latin Name: *Hydrangea paniculata*
Varietal Denomination: NCHP1

(71) Applicant: North Carolina State University, Raleigh, NC (US)

(72) Inventors: Thomas Green Ranney, Arden, NC (US); Darren H. Touchell, Arden, NC (US); Andra Windorf Nus, Arden, NC (US); Irene Palmer, Arden, NC (US); Nathan Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/845,453

(22) Filed: Jan. 6, 2023

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Hydrangea paniculata* plant named 'NCHP1' is disclosed, characterized by a compact, rounded habit with thick stems. Extremely abundant, white sterile flowers in large, broadly pyramidal panicles that open white and fade to green. The new variety is a *Hydrangea*, typically produced as an outdoor ornamental plant.

3 Drawing Sheets

Latin name of the genus and species: The Latin name of the novel plant variety disclosed herein is *Hydrangea paniculata.*

Variety denomination: The inventive seedling of *Hydrangea paniculata* disclosed herein has been given the varietal denomination 'NCHP1'. Prior to the designation of the varietal denomination, 'NCHP1' was referred to by its experimental code: H2013-127-009.

BACKGROUND OF THE INVENTION

The present invention comprises a new and distinct panicle *Hydrangea* cultivar hereinafter referred to by the cultivar name 'NCHP1'. This new *Hydrangea* was developed through a breeding program in Mills River, N.C. 'NCHP1' was selected during the Summer of 2015 from a group of seedlings created by the controlled pollination of female parent *Hydrangea paniculata* H2008-081-010 (unpatented) and male/pollen parent *Hydrangea paniculata* 'Phantom' (unpatented). The crossing resulting in the new variety was conducted during the Summer of 2012.

The first asexual propagation of 'NCHP1' was carried out in July 2015 by rooting stem cuttings at a research greenhouse in Mills River, N.C. and has been asexually reproduced repeatedly by vegetative cuttings over a 7-year period. 'NCHP1' roots readily from softwood cuttings treated with a basal dip of 3,000-4,000 ppm indole butyric acid (potassium salt) in water. 'NCHP1' has been found to retain its distinctive characteristics through successive asexual propagations.

SUMMARY OF THE INVENTION

The following are the unique combination of characteristics of this new cultivar when grown under standard horticultural practices in Mills River, N.C.

1. A compact, rounded habit with thick stems.
2. Extremely abundant, white sterile flowers in large, broadly pyramidal panicles that open white and fade to green.
3. An additional flush of sterile lowers from the top of the panicle later in the flowering season providing an extended season of bloom from July to October.

PARENT COMPARISONS

Plants of the new cultivar *Hydrangea paniculata* 'NCHP1' can be compared to the seed parent, the unpatented *Hydrangea paniculata* H2008-081-010. Plants of 'NCHP1' are similar to plants of the seed parent in most horticultural characteristics, however, plants of 'NCHP1' differ in the following:

1. Plants of the new variety have rounded, compact habits, while plants of the seed parent have large, vase-shaped habits.
2. The new variety produces white sterile flowers in broad, pyramidal panicles. The seed parent produces fewer sterile flowers, in an elongated panicle.
3. The new variety produces a flush of sterile flowers from the top of the panicle late in the flowering season. This characteristic has not been seen in the seed parent.

Plants of the new cultivar *Hydrangea paniculata* 'NCHP1' can be compared to the pollen parent, *Hydrangea paniculata* 'Phantom', unpatented. Plants of 'NCHP1' are similar to plants of the pollen parent in most horticultural characteristics, however, plants of 'NCHP1' differ in the following:

1. Plants of the new variety have rounded, compact habits, while plants of the seed parent have large, vase-shaped habits.

2. The new variety produces white sterile flowers that fade to green. The pollen parent produces white flowers that fade to a soft pink.
3. The new variety produces a flush of sterile flowers from the top of the panicle late in the flowering season. This characteristic has not been seen in the pollen parent.

COMMERCIAL COMPARISONS

Plants of the new cultivar *Hydrangea paniculata* 'NCHP1' can be compared to the commercial variety, *Hydrangea paniculata* 'ILVOBO', U.S. Plant Pat. No. 22,782. Plants of 'NCHP1' are similar to plants of the commercial variety in most horticultural characteristics, however, plants of 'NCHP1' differ in the following:

1. Plants of the new variety are larger than plants of this comparator.
2. Plants of the new variety have a compact, rounded habit, while plants of this comparator are compact, upright, and mounded.
3. Initial sterile sepal color of the new variety is green-white, while the initial sepal color of this comparator is white.
4. Sterile sepals of the new variety fade to yellow-green, while sterile sepals of this comparator fade to red-purple.

Plants of the new cultivar *Hydrangea paniculata* 'NCHP1' can be compared to the commercial variety, *Hydrangea paniculata* 'Limelight', U.S. Plant Pat. No. 12,874. Plants of 'NCHP1' are similar to plants of the commercial variety in most horticultural characteristics, however, plants of 'NCHP1' differ in the following:

1. Plants of the new variety are smaller than plants of this comparator.
2. Plants of the new variety have a compact, rounded habit, while plants of this comparator are upright and mounded.
3. Initial sterile sepal color of the new variety is green-white, while the initial sepal color of this comparator is yellow-green.
4. Sterile sepals of the new variety fade to a lighter yellow-green than sterile sepals of this comparator.

BRIEF DESCRIPTION OF THE PHOTOGRAPHS

This new *Hydrangea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Hydrangea*.

DETAILED BOTANICAL DESCRIPTION

Figure 1:
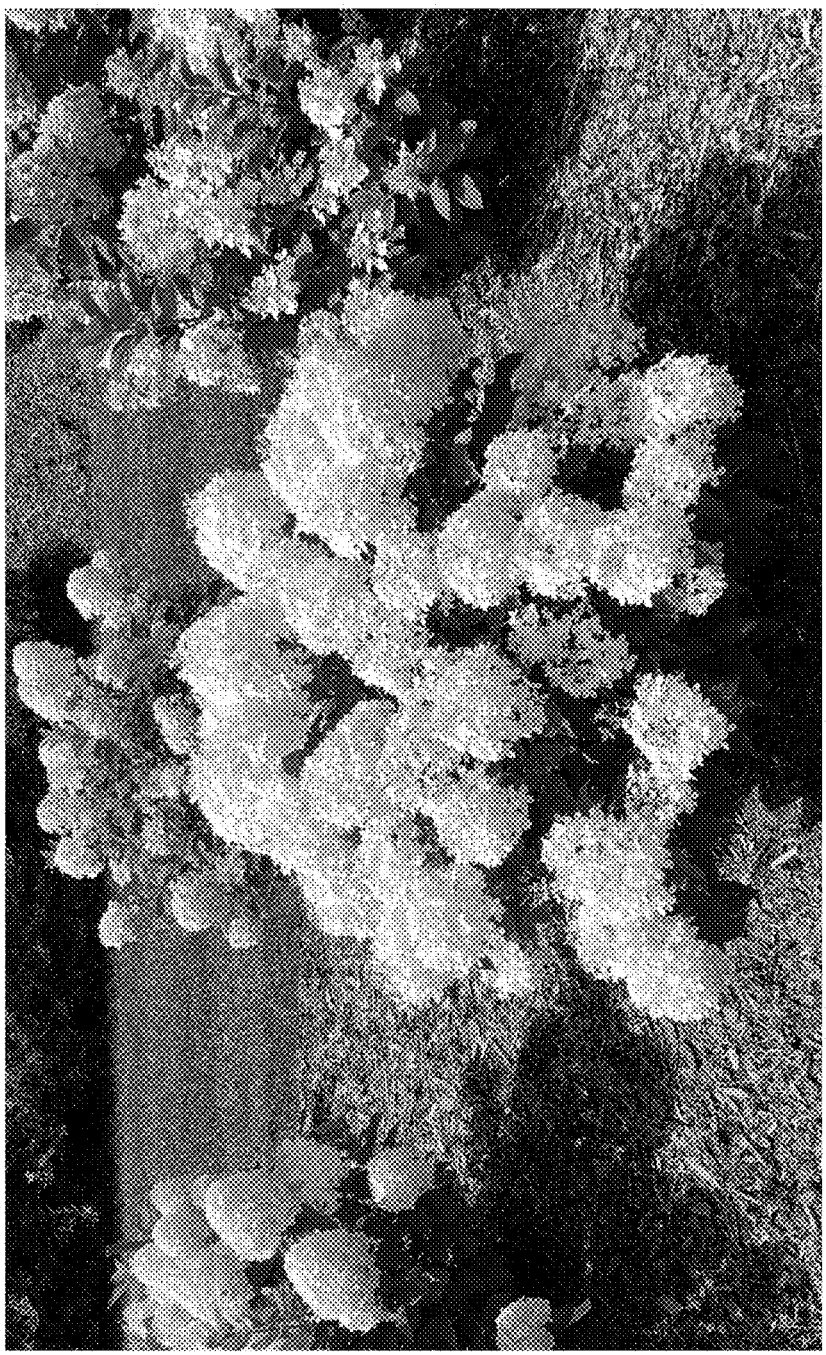
FIG. 1 is a color photograph showing the compact habit of a field-grown plant in summer of 2021, in Mills River, N.C. The plant is approximately 2 years old.
Figure 2:
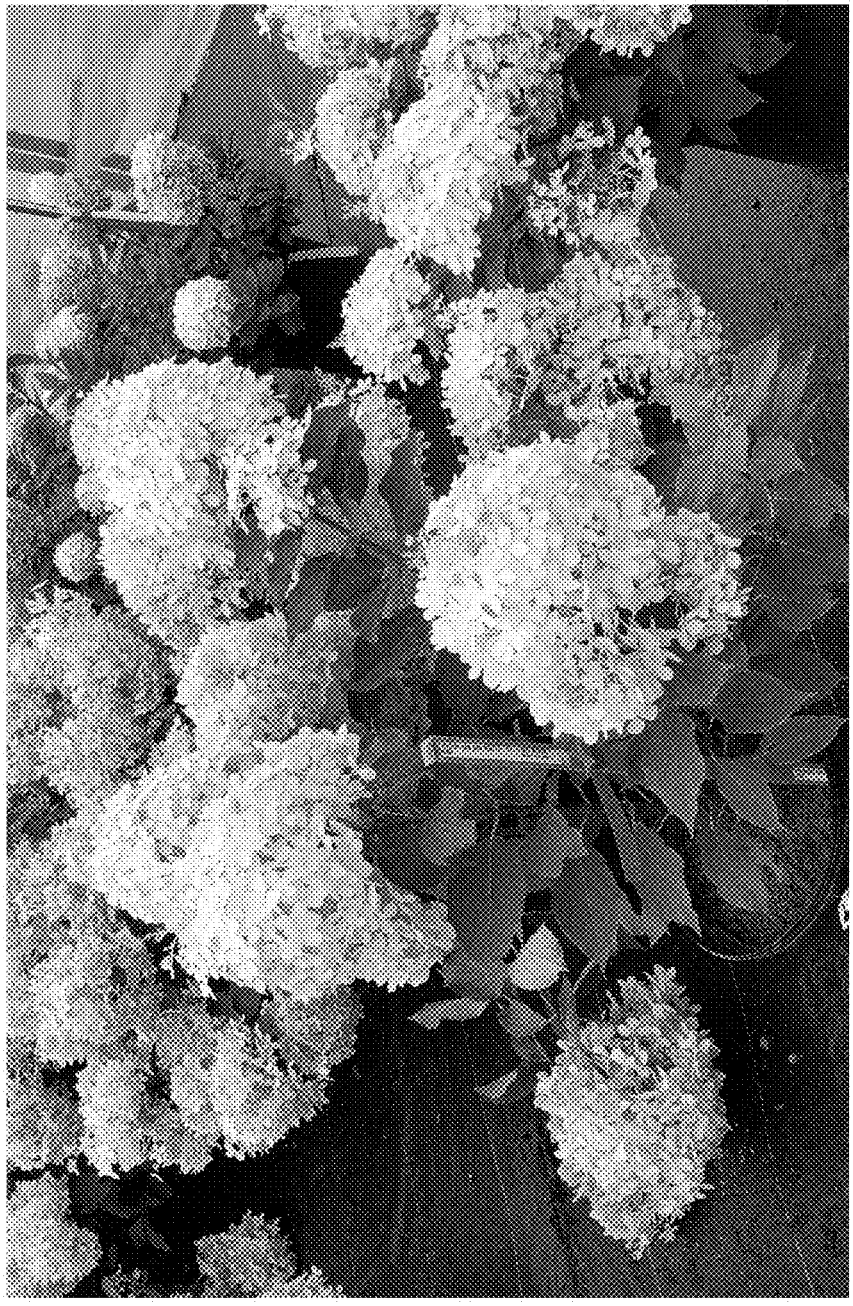
FIG. 2 is a color photograph showing the dense inflorescences with numerous sterile florets of 'NCHP1' in summer of 2021, in Mills River, N.C. Plants are container grown and approximately 1.5 years old.
Figure 3:
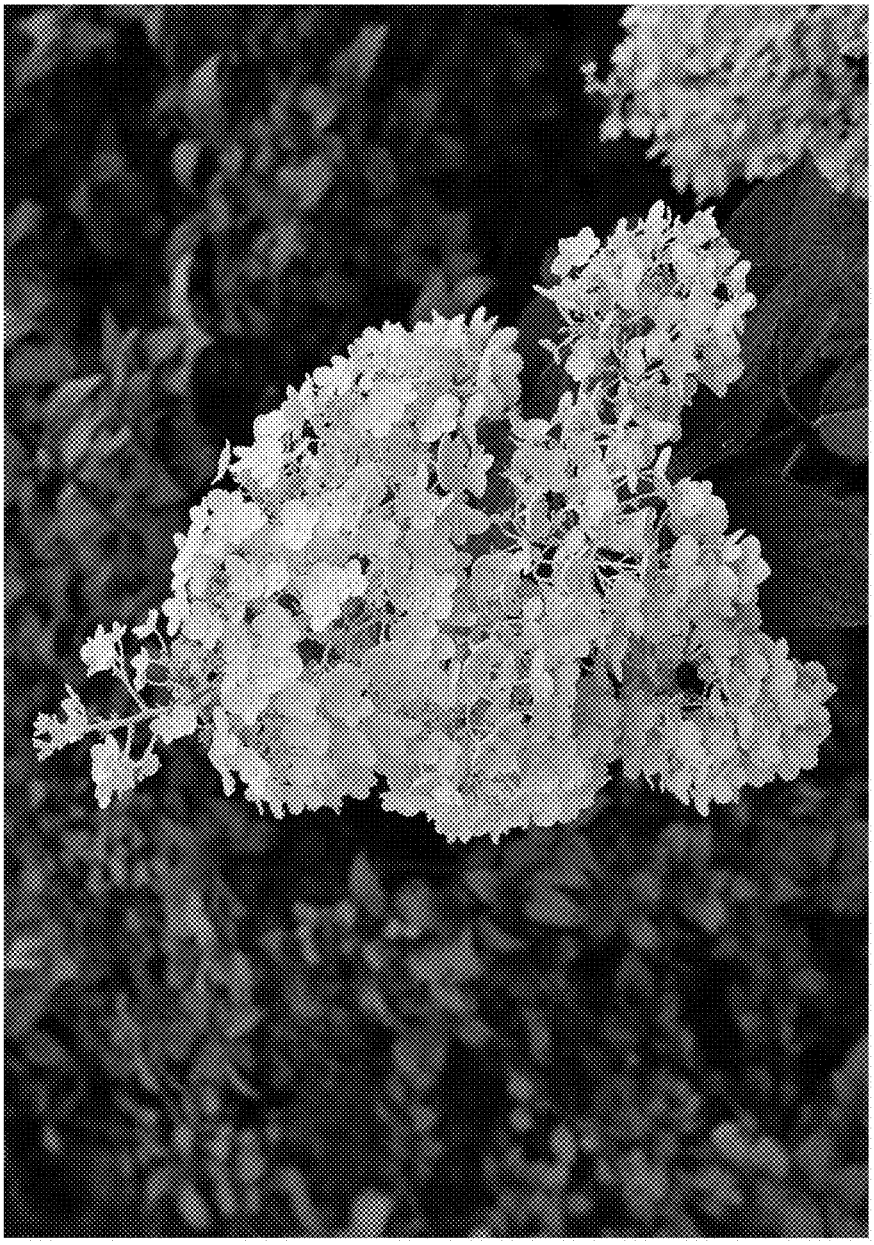
FIG. 3 is a color photograph of the broad panicles of the inflorescences and the clean foliage of 'NCHP1' in summer of 2021, in Mills River, N.C.

The following is a detailed description of the botanical characteristics of the new and distinct panicle *Hydrangea* cultivar known by the denomination 'NCHP1'. The detailed description was taken on a five-year-old field-grown plant in Mills River, N.C. in 2021. All colors cited herein refer to The Royal Horticultural Society Colour Chart (The Royal Horticultural Society (RHS), London, Sixth Edition). Where specific dimensions, sizes, colors, and other characteristics are given, it is to be understood that such characteristics are approximations or averages set forth as accurately as practicable.

Classification:

*Botanical name.*—*Hydrangea paniculata* 'NCHP1'.

*Common name.*—Panicle *Hydrangea.*

Plant description:

*Growth habit.*—Rounded, upright.

*Height.*—90 to 150 cm.

*Width.*—90 to 150 cm.

Stems, shoots, branches, trunk:

*Shoots* (*current year's growth*).—Shape: Rounded. Shoot length: Avg. 9.8 cm (Range 6 to 16 cm). Shoot diameter: Avg. 0.25 cm (0.2 to 0.4 cm). Color: Light Yellow Green (RHS 138D). Texture: Pubescent.

*Shoots* (*prior year's growth*).—Shape: Rounded. Stem length: Avg. 20.7 (8 to 35 cm). Stem diameter: Avg. 0.4 cm (0.3 to 0.5 cm). Color: Greyish Brown (RHS 166A). Texture: Pubescent.

*Branches* (*woody branches* 2-4 *years old*).—Shape: Rounded. Branch length: Avg. 29.4 cm (14 to 40 cm). Branch diameter: Avg. 1.6 cm (0.6 to 2.8 cm). Color: Light Olive Grey (RHS 197A). Texture: Glabrous, with vertical fissures.

*Internode length.*—Avg. 7.8 cm (4.5 to 11 cm).

Leaves:

*Type.*—Simple.

*Persistence.*—Deciduous.

*Arrangement.*—Opposite, sometimes in whorls of 3.

*Shape.*—Ovate.

*Venation.*—Pinnate. Vein color, upper and lower: Light Yellow Green (RHS 138D).

*Length of lamina.*—Avg. 8.0 cm (5.5 to 10.5 cm).

*Width.*—Avg. 4.4 cm (3.1 to 6.5 cm).

*Color, both emerging and mature.*—Upper: Moderate Olive Green (RHS 137B). Lower: Moderate Yellow Green (RHS 147C).

*Texture.*—Upper: Glabrous. Lower: Sparsely pubescent.

*Apex.*—Acuminate.

*Base.*—Acute.

*Margins.*—Serrate.

*Leaf attachment.*—Petiolate.

*Petiole.*—Length: Avg. 1.4 cm (0.9 to 2 cm). Diameter: Avg 0.15 (0.1 to 0.2 cm). Color: Light Yellow Green (RHS 138D). Texture: Pubescent.

Inflorescence:

*Description.*—Flowers arranged in terminal, broadly pyramidal panicles, composed of fertile and sterile flowers.

*Flowering season.*—July to October in Mills River, N.C.

*Number of inflorescences per plant.*—More than 300.

*Number of flowers per inflorescence.*—More than 600.

*Fragrance.*—Light, sweet fragrance.

*Inflorescence.*—Height: Avg. 13.7 cm (12.0 to 16.5 cm), terminal of the panicle extends an additional 3.0 to 4.0 cm above the panicle as inflorescence ages.

Diameter at the widest point of inflorescence: Avg. 17.4 cm (15.0 to 20.5 cm).

*Flower bud, fertile and sterile flowers.*—Shape: Ovoid. Length: About 0.3 cm. Diameter: About 0.2 cm. Color: Greenish White (RHS 155C). Texture: Glabrous.

*Flower.*—Fertile flower diameter: About 0.8 cm. Fertile flower height: About 0.6 cm. Sterile flower diameter: Avg. 3.0 cm (2.3 to 3.4 cm). Sterile flower height: About 0.7 cm.

*Petals, fertile flowers.*—Arrangement: Whorled. Number of petals per fertile flower: 5. Shape: Ovate-lanceolate. Length: About 0.3 cm. Width: About 0.15 cm. Color: Greenish White (RHS 157D). Texture: Glabrous. Apex: Obtuse. Base: Obtuse. Margin: Entire.

*Sepal, fertile flowers.*—Number: 5. Arrangement: Whorled. Shape: Ovate. Length: Less than 0.1 cm. Width: About 0.1 cm. Color: Greenish White (RHS 157D). Texture: Glabrous. Apex: Acute. Base: Fused. Margin: Entire.

*Sepal, sterile flowers.*—Number: 4-5. Arrangement: Whorled. Shape: Elliptical. Length: Avg. 1.3 cm (0.9 to 1.6 cm). Width: Avg. 0.8 cm (0.7 to 1.0 cm). Color: Greenish White (RHS 157D) fading to Light Yellow Green (RHS 145D). Texture: Glabrous. Apex: Rounded. Base: Acute. Margin: Entire.

*Peduncle.*—Length: Avg. 7.5 cm (5 to 9 cm). Diameter: About 0.15 cm. Color: Greenish White (RHS 157D). Texture: Pubescent.

*Pedicels, fertile flowers.*—Length: About 0.2 cm. Diameter: About 0.1 cm. Color: Greenish White (RHS 157D). Texture: Pubescent.

*Pedicels, sterile flowers.*—Length: Avg. 2.0 cm (1.4 to 2.3 cm). Diameter: About 0.1 cm. Color: Greenish White (RHS 157D). Texture: Pubescent.

Reproductive organs:

*Fertile flowers.*—Gynoecium: Pistil number: 3 fused. Pistil length: Less than 0.1 cm. Stigma shape: Rounded. Stigma color: Greenish White (RHS 157D). Style length: Less than 0.1 cm. Style color: Greenish White (RHS 157D). Androecium: Stamen number: 9-10. Anther shape: Bilobed. Anther size: About 0.1 cm. Anther color: Greenish White (RHS 157D). Amount of pollen: Scarce. Pollen color: Greenish White (RHS 157D).

OTHER CHARACTERISTICS

Fruit and seed: None observed.

Disease and insect resistance: No significant disease or insect pests have been observed.

Cold hardiness: At least USDA zone 6b; testing has not been completed in colder zones.

What is claimed is:

1. A new and distinct cultivar of *Hydrangea* plant named 'NCHP1' as illustrated and described herein.

* * * * *